United States Patent [19]

Sekiguchi et al.

[11] Patent Number: 4,762,410
[45] Date of Patent: Aug. 9, 1988

[54] OPHTHALMIC INSTRUMENT

[75] Inventors: Kyoji Sekiguchi, Tokyo; Isao Matsumura, Yokosuka; Haruhisa Madate, Kawasaki, all of Japan

[73] Assignee: Canon Kabushiki Kaisha, Tokyo, Japan

[21] Appl. No.: 4,822

[22] Filed: Jan. 12, 1987

Related U.S. Application Data

[63] Continuation of Ser. No. 596,412, Apr. 3, 1984.

[30] Foreign Application Priority Data

Apr. 7, 1983 [JP] Japan .................................. 58-61415
Apr. 7, 1983 [JP] Japan .................................. 58-61416
Apr. 7, 1983 [JP] Japan .................................. 58-61417

[51] Int. Cl.$^4$ .......................................... A61B 13/14
[52] U.S. Cl. ...................................... 351/206; 351/209
[58] Field of Search ............... 351/205, 206, 210, 209

[56] References Cited

U.S. PATENT DOCUMENTS 4,149,787 4/1979 Kobayashi et al. ................. 351/206
4,486,080 12/1984 Itoh et al. ............................. 351/206

*Primary Examiner*—Rodney B. Bovernick
*Assistant Examiner*—P. M. Dzierzynski
*Attorney, Agent, or Firm*—Fitzpatrick, Cella, Harper and Scinto

[57] ABSTRACT

Disclosed is an ophthalmic instrument provided with an illuminating system for illuminating an eye being examined, an imaging system for imaging a predetermined portion of the eye being examined at a predetermined image plane position, and a detecting system for detecting any variation in the reflected light from the front-eye-part of the eye being examined by a nictitation of the eye being examined without depending on the quantity of illuminating light of the illuminating system.

8 Claims, 11 Drawing Sheets

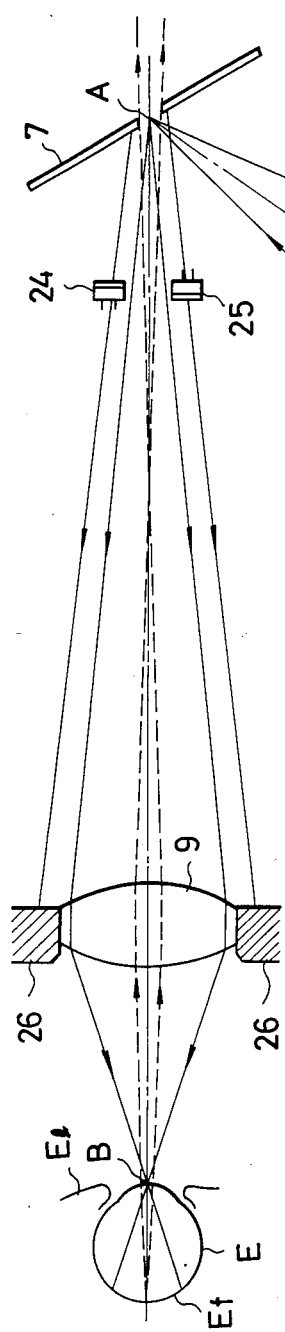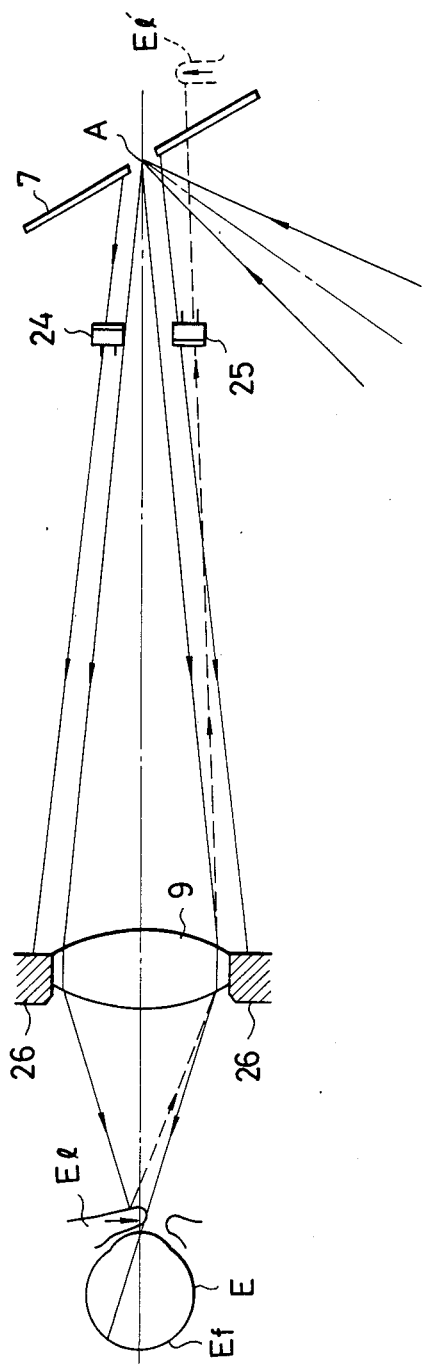

FIG.18
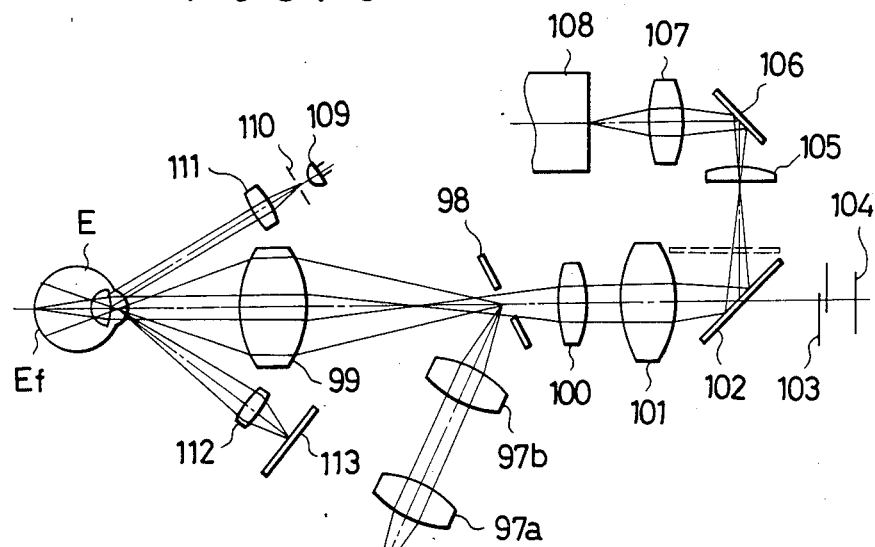
FIG.19
FIG.20
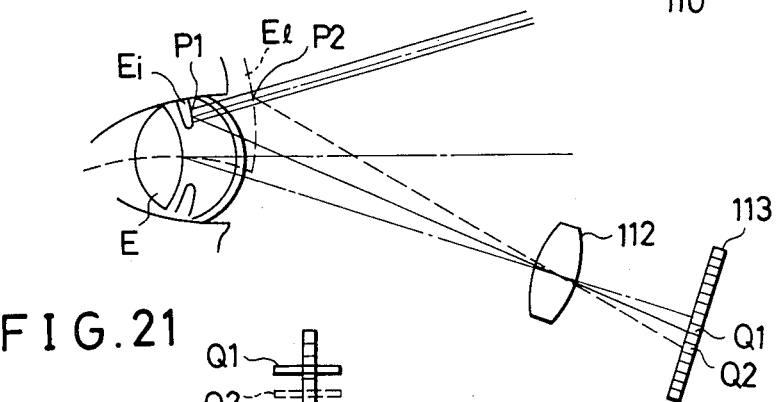
FIG.21

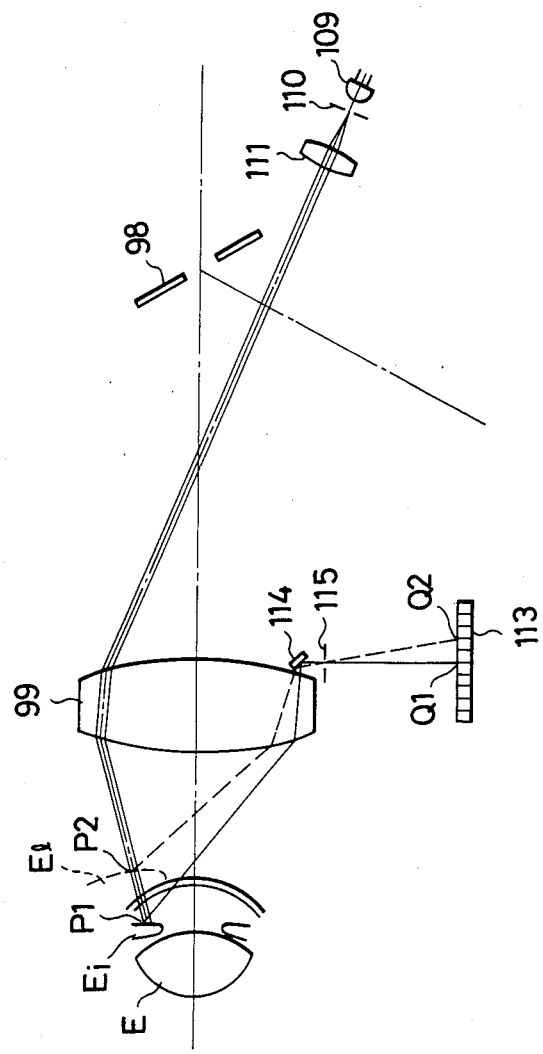

OPHTHALMIC INSTRUMENT this application is a continuation of application Ser. No. 596,412 filed 4/3/84.

BACKGROUND OF THE INVENTION

1. Field of the Invention

This invention relates to an eye-fundus camera, and more particularly to an ophthalmic instrument for detecting a nictitation i.e., winking of an eye being examined.

2. Description of the Prior Art

In recent years, eye-fundus cameras have been widely used in connection with the prevention of adult diseases. Above all, eye-fundus cameras are often used for group medical examinations and, in group medical examinations, the routine examination is usually practiced in a manner which the fundus of each of the right and left eyes is photographed once, but if the examinee nictitates during photography, the fundus of each of the examinee's eyes cannot be accurately photographed. Particularly, in a non-mydriatic eye-fundus camera, once the photographing light is emitted, the eye being examined effects miosis and therefore cannot be immediately re-photographed and further, the photographer may sometimes overlook the nictitation of the examinee resulting in a great inconvenience. As a nictitation detecting method, there is known a method of comparing the increment of any variation in the reflected light from the fundus of the eye being examined illuminated by the eye fundus illuminating light caused by a nictitation with a reference level and detecting the nictitation, as shown in Japanese Laid-open Patent Application No. 69617/1977. However, the eye fundus illuminating light is not constant from person to person due to the differences in the transmission factor in the eyeball and in the size of the pupil diameter. Accordingly, if this reference level is fixed, the reflected light will be too strong or too weak depending on the magnitude of the quantity of illuminating light and this leads to a problem that the nictitation cannot be detected normally. Further, there is a disadvantage that the photographing light will be emitted if the eye being examined nictitates after the photographer has depressed the photographing switch.

SUMMARY OF THE INVENTION

It is an object of the present invention to provide an ophthalmic instrument which is capable of detecting any variation in the reflected light from the front-eye-part by a nictitation of an eye being examined without depending on the quantity of illuminating light directed at the eye fundus or the like to thereby accurately detect the nictitation.

It is a further object of the present invention to provide an ophthalmic instrument which is capable of automatically detecting a nictitation by one or a combination of the variation in quantity of reflected light, the variation in position of the reflected light and the variation in open state of the pupillary zone which are caused by the nictitation and thereby stopping the subsequent operation of the instrument.

The invention will become fully apparent from the following detailed description thereof taken in conjunction with the accompanying drawings.

BRIEF DESCRIPTION OF THE DRAWINGS

FIG. 2 illustrates the eye being examined when its eyelid is open.

FIG. 3 illustrates the eye being examined when its eyelid is closed.

FIG. 18 shows the optical arrangement of a third embodiment of the present invention.

FIG. 19 is a front view of a mask.

FIG. 20 illustrates the operation of a nictitation detecting mechanism.

FIG. 21 illustrates the movement of the image on a line sensor.

FIG. 22 shows the optical arrangement of another embodiment of the nictitation detecting mechanism.

DETAILED DESCRIPTION OF THE PREFERRED EMBODIMENTS

Figure 1:
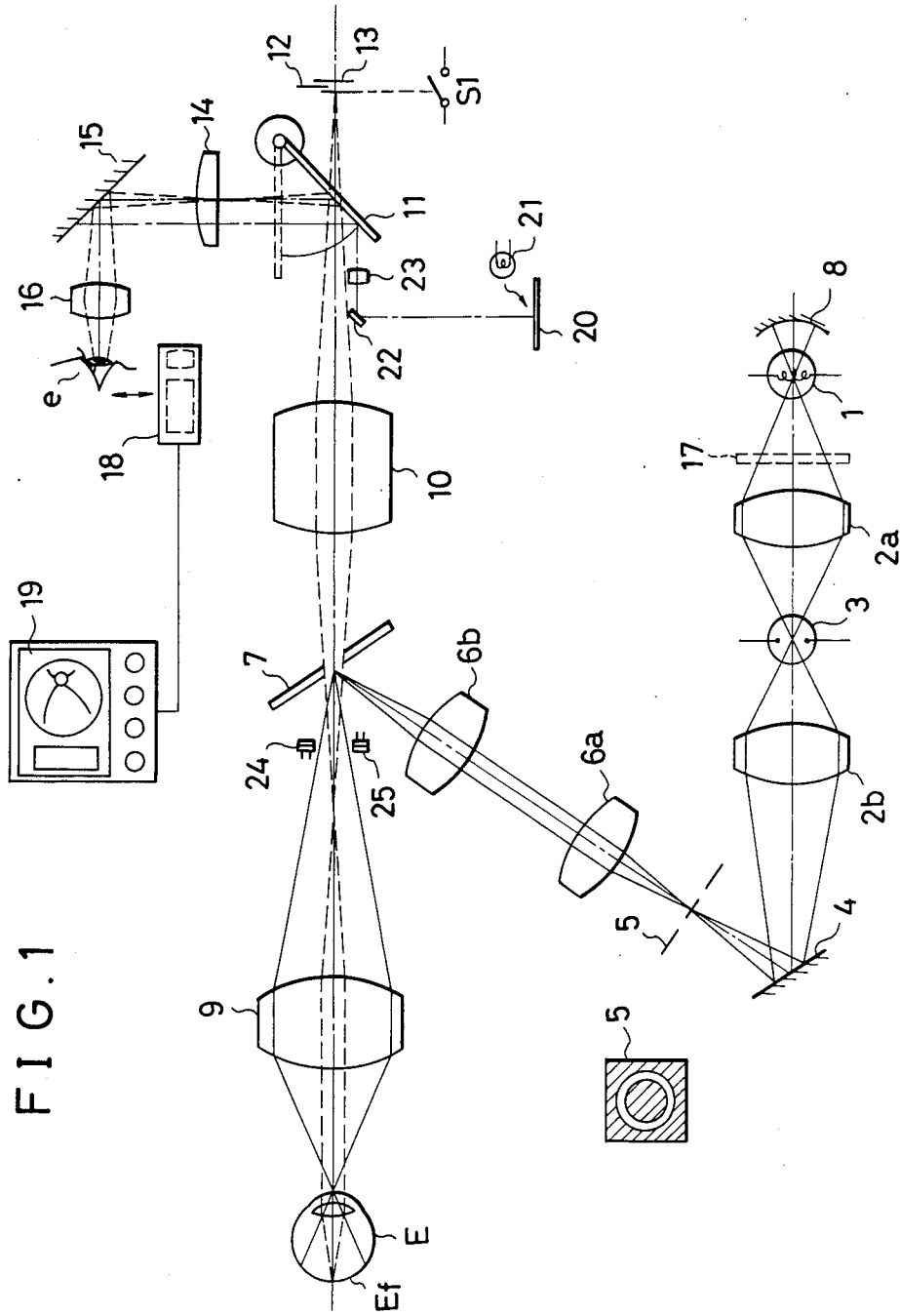
FIG. 1 shows the construction of the optical system of a first embodiment of the present invention.

Referring to FIG. 1 which shows an embodiment of the optical system of an eye-fundus camera, reference numeral 1 designates an observation light source comprising a tungsten lamp or the like. The light emitted from the observation light source 1 enters a mirror 4 through a condenser lens 2a, a photographing light source 3 comprising a xenon discharge tube or the like, and a condenser lens 2b, and is deflected by the mirror 4 and arrives at an apertured mirror 7 via a ring slit plate 5 and relay lenses 6a and 6b. Designated by 8 is a reflecting mirror disposed behind the observation light source 1 to condense and reflect the light of the observation light source 1.

The light having entered the apertured mirror 7 from the above-described illuminating optical system is reflected toward an eye E being examined by the apertured mirror 7, illuminates the fundus Ef of the eye E being examined, travels back along the original optical path, is further transmitted through the apertured mirror 7 and comes to the observation optical system. An objective lens 9 is disposed between the apertured mirror 7 and the eye E being examined, and a photographing lens 10, a jump-up mirror 11, a shutter 12 and a photographing film 13 are successively arranged behind the apertured mirror 7 along the optic axis. On the reflection side of the jump-up mirror 11, a field lens 14 placed at a position conjugate with the photographing film 13, a mirror 15 for deflecting the optical path and a finder lens 16 are successively disposed along the optic axis. Letter e designates the photographer's eye.

In a group medical examination, a method which illuminates the eye fundus Ef by infrared light and which does not use a mydriatic agent is often used, and an infrared filter 17 is inserted between the observation light source 1 and the condenser lens 2a. In this case, infrared light cannot be sensed by the naked eye and therefore, a photographing tube 18 for infrared ray is disposed at the position of the photographer's eye e so that infrared light is observed by means of a TV monitor 19. The image of the eye fundus Ef and the content of an ID card 20 on which the name, etc. of the examinee are written are displayed on the TV monitor 19. Reference numeral 21 designates a light source for illuminating the ID card 20, and a mirror 22 and a lens 23 are optical members for directing the content of the ID card 20 to the jump-up mirror 11. Further, an illuminating light receiving sensor 24 for receiving the illuminating light from the apertured mirror 7 and a reflected light receiving sensor 25 for receiving the reflected light when the eyelid of the eye E being examined is open are provided between the apertured mirror 7 and the objective lens 9. In these light receiving sensors 24 and 25, visible and infrared rays are used as the illuminating light and therefore, sensors having the peak of sensitivity in the infrared range are preferred.

In this eye-fundus camera, the illuminating light source 1 and the photographing light source 3 are substantially conjugate with respect to the condenser lens 2a, and during observation, the observation light source 1 is turned on and during photography, the photographing light source 3 is momentarily turned on. The light source image is once formed near the ring slit plate 5 by the condenser lens 2b, and then the image of the annular opening of the ring slit plate 5 is formed near the apertured mirror 7 by the relay lenses 6a and 6b and there, the illuminating light is reflected and travels to the left. The eye fundus Ef is illuminated after the image of the annular opening has been formed near the cornea of the eye E being examined by the objective lens 9.

The reflected light from the eye fundus Ef travels to the right and is once imaged by the cornea and the objective lens 9, and then passes through the apertured mirror 7 and is imaged by the photographing lens 10. During the observation by the naked eye, the eye fundus image is directed upwardly by the jump-up mirror 11 which is in its solid-line position, and is observed by the photographer's eye e through the finder lens 16 and, during photography, the jump-up mirror 11 is rotated to its dotted-line position and the eye fundus image is formed on the photographing film 13 via the opened shutter 12.

Where observation is effected by the use of infrared light with the infrared filter 17 being inserted in the illuminating optical system, the eye fundus image is projected onto the TV monitor 19 by the photographing tube 18 for infrared ray. At this time, the content of the ID card 20 is illuminated by the illuminating light source 21, is directed upwardly by the jump-up mirror 11 through the mirror 22 and the lens 23 and is displayed with the eye fundus image on the TV monitor 19. Also, the presence of the light flux which illuminates the eye fundus Ef is confirmed by the illuminating light receiving sensor 24 and the closed state of the eyelid of the eye E being examined is confirmed by the reflected light receiving sensor 25.

FIG. 2 shows the open state of the eyelid of the eye E being examined. The objective lens 9 is held by a barrel 26, and the illuminating light flux passes through the opened eyelid El of the eye E being examined to the eye fundus Ef as indicated by solid lines, and the photographing light flux returns as indicated by dotted lines. The point A on the apertured mirror 7 and the point B on the eye E being examined are made conjugate with respect to the objective lens 9. The light receiving surface of the illuminating light receiving sensor 24, as shown in FIG. 2, is disposed at a position capable of receiving part of the illuminating light flux, and faces in the direction opposite to the eye E being examined, and the light receiving surface of the reflected light receiving sensor 25 faces in the direction of the eye E being examined. The illuminating light receiving sensor 24 and the reflected light receiving sensor 25 are both disposed outside the maximum photographing light flux.

FIG. 3 shows a state in which the eyelid El has made half-nictitation, and the virtual image El' thereof is formed at a position conjugate with the eyelid El.

Figure 4:
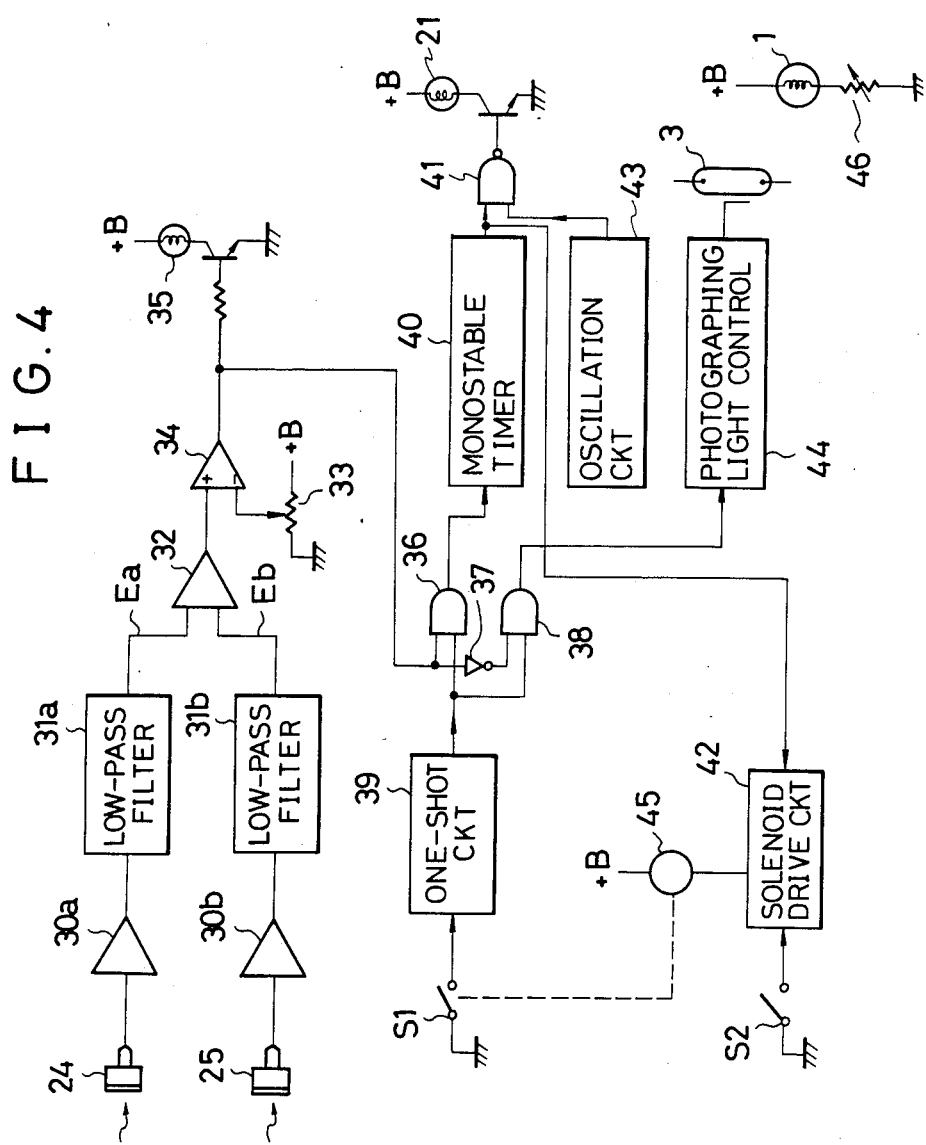
FIG. 4 is a block diagram of an electrical control circuit.

FIG. 4 shows an embodiment of the electrical control circuit. The outputs of the light receiving sensors 24 and 25 are input as outputs Ea and Eb to a divider circuit 32 via amplifiers 30a and 30b, respectively. The output of the divider circuit 32 which operates Ea/Eb is input to a comparator 34 with the output of a reference value 33, and the output of the comparator 34 is delivered to a lamp 35 for displaying the open state and the closed state of the eyelid of the eye E being examined and is connected to a first AND circuit 36 and to a second AND circuit 38 through a "not" circuit 37. The pulse output of a one-shot circuit 39 operable in response to the signal from a synchro switch S1 is input to the first and second AND circuits 36 and 38. The output of the first AND circuit 36 is input to a monostable timer circuit 40, the output of which is transmitted to a NAND circuit 41 and a solenoid drive circuit 42. The output from an oscillation circuit 43 is also input to the NAND circuit 41, the output of which may drive the light source 21 for illuminating the ID card 20. The output of the second AND circuit 38 may operate the photographing light source 3 via a photographing light source control circuit 44. Reference character S2 designates a photographing switch, the output of which is supplied to the solenoid drive circuit 42, from which a signal is transmitted to a solenoid 45 for operating the switch S1. Designated by 46 is a variable resistor for increasing or decreasing the intensity of illumination of the observation light source 1.

In the above-described construction, the conjugate image of the apertured mirror 7 is formed near the cornea of the eye E being examined by the illumination of the observation light source 1, but as shown in FIG. 2, the illuminating light is applied only to the surface of the cornea when the eyelid is open. At this time, the light entering the reflected light receiving sensor 25 is only the reflected light by the barrel 26 and therefore is several times less than the light entering the illuminating light receiving sensor 24. However, when the examinee nictitates, the eyelid El lowers to intercept the illuminating light as shown in FIG. 3 and therefore, the reflected light from the eyelid El travels toward the virtual image El' which lies at a position conjugate with the eyelid El. This reflected light, as indicated by a dotted line in FIG. 3, travels outside the illuminating light flux near the apertured mirror 7 and enters the reflected light receiving sensor 25.

Figure 5:
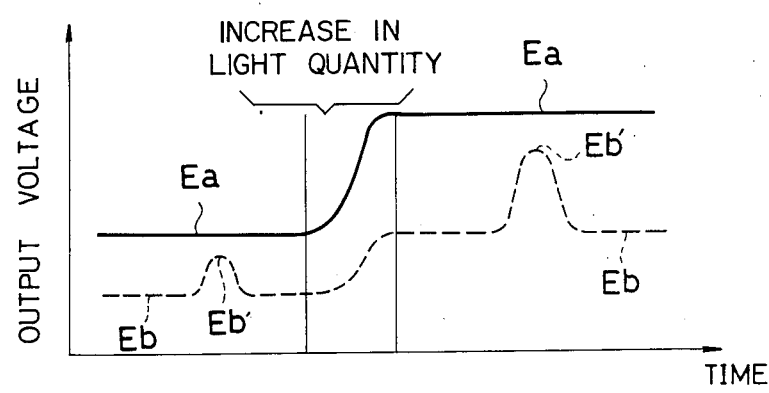
FIG. 5 is a graph showing the relation between the illuminating light and the reflected light when the quantity of illuminating light is increased.

Among the output Ea after the low-pass filter 31a of the illuminating light receiving sensor 24 when the eyelid is open, the output Eb after the low-pass filter 31b of the reflected light receiving sensor 25 when the eyelid is open and the outputs Ea' and Eb' when the eyelid is closed, there are established the following relations:

$$Ea = Ea'$$

$$Ea = k1 \cdot Eb$$

$$Eb' = k2 \cdot Eb$$

where k1 and k2 are constants (k1>1, k2>1), and these relations before and after the quantity of illuminating light of the observation light source 1 is increased become such as shown in FIG. 5. This is because the illuminating light receiving sensor 24 faces in a direction opposite to the eye E being examined and is not affected by the reflected light from the eyelid El that the output of the illuminating light receiving sensor 24 is the same when the eyelid is open and when the eyelid is closed, that is, Ea=Ea' is established at all times. These relations are established as shown in FIG. 5 even if the quantity of reflected light is varied. Accordingly, if the ratio between the outputs of the illuminating light receiving sensor 24 and the reflected light receiving sensor 25 is obtained and the reference value is set to a value slightly less than the value of the ratio when the eyelid is closed, it will be possible to detect the closed state of the eyelid even if the quantity of illuminating light is varied.

Description will now be made of the operation of the electrical control circuit shown in FIG. 4. The illuminating light is received by the illuminating light receiving sensor 24 and amplified by the amplifier 30a, and the power source frequency component or the like contained in the illuminating light is removed by the low-pass filter 31a, and the illuminating light is input to the divider circuit 32. On the other hand, the reflected light from the eyelid El is received by the reflected light receiving sensor 25, passes through the amplifier 30b and the low-pass filter 31b and is likewise input to the divider circuit 32. The output which is the ratio between Ea and Eb from the divider circuit 32 is compared with the reference value 33 by the comparator 34 and, when the output of the divider circuit 32 becomes greater than the reference value 33, the comparator 34 puts out a Hi level logic output. That is, at this time, the eye E being examined is nictitating and the lamp 35 is turned on. The reference value 33 may be set to a value somewhat smaller than the output of the divider circuit 32 when the eyelid of the eye E being examined is open. The comparator 34 puts out a Lo level state or a Hi level state depending on the open state or the closed state of the eyelid of the eye E being examined.

When the photographer adjusts the focus to the fundus Ef of the eye E being examined and closes the photographing switch S2, the solenoid drive circuit 42 is operated to drive the solenoid 45 and the jump-up mirror 11 jumps up, and further the shutter 12 is opened and the synchro switch S1 conducts. The conduction signal from the switch S1 is input to the one-shot circuit 39 and a pulse corresponding to the leading edge of the conduction signal is put out. This pulse is input to the first AND circuit 36 and the second AND circuit 38 and the logic product of the pulse and the signal from the comparator 34 is taken.

If the eyelid of the eye E being examined is open, the output from the comparator 34 is at a Lo level and is inverted into a Hi level by the "not" circuit 37 and the second AND circuit 38 becomes active, and a pulse from the one-shot circuit 39 passes through the second AND circuit 38 and is input to a stroboscopic drive circuit 44 to thereby cause the photographing light source 3 to emit light and thus, the eye fundus Ef is photographed on the film 13.

However, when the eye E being examined nictitates, the output of the comparator 34 assumes a Hi level and the first AND circuit 36 becomes active, and a pulse from the one-shot circuit 39 passes through the first AND circuit 36 and is input to the monostable timer circuit 40, which thus puts out a Hi level signal for several seconds. During the time that the signal from this timer circuit 40 is at a Hi level, the NAND gate 41 puts out the signal from the oscillator 43 and turns on and off the lamp 21 for illuminating the ID card 20. Since the photographer is observing the ID card 20 illuminated by this illuminating lamp 21 with the eye fundus Ef, he can know from the turn-on-and-off of the image of the ID card 20 that the eye E being examined has nictitated. The illuminating lamp 21 continues to be turned on because normally the output of the monostable timer circuit 40 is at a Lo level. The signal from the monostable timer circuit 40 is input also to the solenoid drive circuit 42 and, during the time that this signal is at a Hi level, that is, during the time that the nictitation is detected and displayed, an inhibiting operation is exerted on the drive circuit 42 so as to prevent the solenoid 45 from operating even if the photographing switch S2 is depressed.

In this control circuit, whether the eyelid of the eye E being examined is closed is discriminated at the timing of the leading edge of the conduction signal of the synchro switch S1 and thus, the nictitation is detected immediately before the photographing light source 3 emits light, and even if the eye E being examined nictitates after the photographing switch S2 has been depressed, the photographing light source 3 will not emit light and the photographer will be aware of the nictitation of the eye being examined by the turn-on-and-off of the lamp 21.

In this embodiment of the control circuit, a subtractor circuit may be used instead of the divider circuit 32. That is, the difference between the output Ea of the illuminating light receiving sensor 24 and the output Eb of the reflected light receiving sensor 25 increases as the quantity of illuminating light is increased. Therefore, if the reference value 33 is set to a value somewhat lower than the output Eb of the reflected light receiving sensor 25 when the eyelid is closed during the minimum quantity of illuminating light, the difference between the outputs of the illuminating light receiving sensor 24 and the reflected light receiving sensor 25 will always be greater than the difference during the minimum quantity of illuminating light even when the quantity of illuminating light is increased and thus, it will become possible to detect the nictitation.

Figure 6:
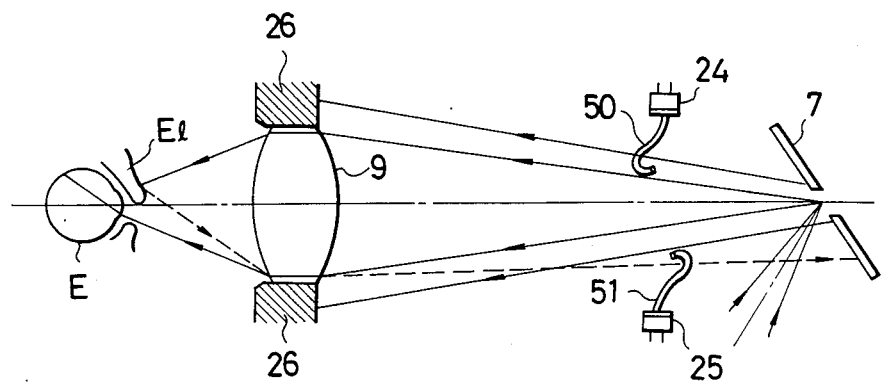
FIGS. 6 and 7 show modifications.
Figure 7:
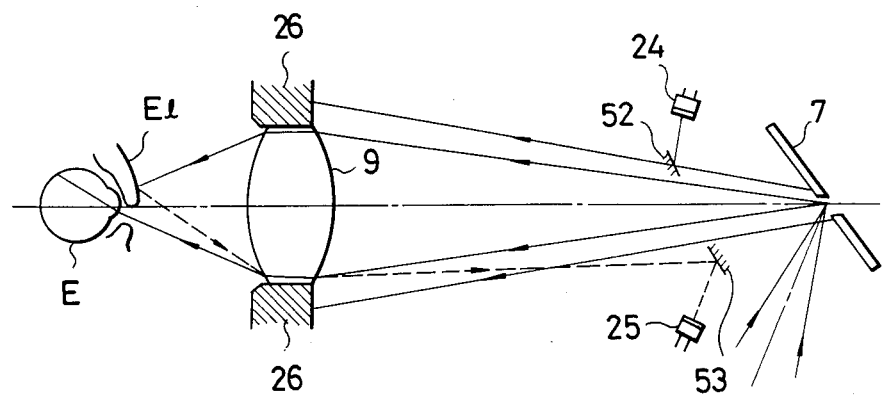

The illuminating light receiving sensor 24 and the reflected light receiving sensor 25 need not always be disposed in the light flux as shown in FIGS. 2 and 3, but as shown, for example, in FIG. 6, optical fibers 50 and 51 may be used so that light fluxes detected at the fore ends of these optical fibers 50 and 51 may be directed to the light receiving sensors 24 and 25, respectively. Alternatively, as shown in FIG. 7, deflecting mirrors 52 and 53 may be disposed in the light flux and the reflected lights therefrom may be directed to the respective light receiving sensors 24 and 25 to obtain a similar effect.

Figure 8:
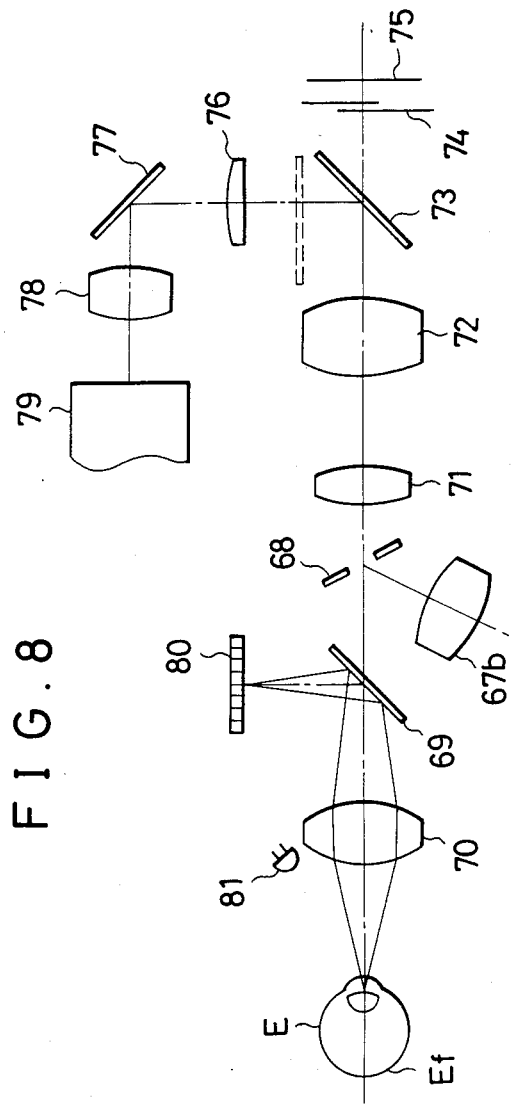
FIG. 8 shows the optical arrangement of a second embodiment of the present invention.

Now, FIG. 8 shows the construction of a second embodiment of the present invention. Reference numeral 61 designates an observation light source comprising a tungsten lamp or the like. The light flux emitted from this observation light source 61 enters a mirror 65 through an infrared filter 62, a condenser lens 63a, a photographing light source 64 comprising a xenon discharge tube or the like, and a condenser lens 63b, and is deflected by the mirror 65 and arrives at an apertured mirror 68 via a ring slit plate 66 and relay lenses 67a and 67b. The light having entered the apertured mirror 68 from the above-described illuminating optical system is reflected toward the eye E being examined by the apertured mirror 68, illuminates the fundus Ef of the eye E being examined, passes along the original optical path and further passes through the apertured mirror 68 to the observation optical system. A beam splitter 69 and an objective lens 70 are disposed between the apertured mirror 68 and the eye E being examined, and a focusing lens 71, a photographing lens 72, a jump-up mirror 73, a shutter 74 and a photographing film 75 are successively arranged behind the apertured mirror 68 along the optic axis. On the reflection side of the jump-up mirror 73, a field lens 76 placed at a position conjugate with the photographing film 75, a mirror 77 for changing the optical path, a TV lens 78 and an image pickup tube 79 are successively disposed along the optic axis. On that side of the beam splitter 69 which reflects the light flux from the eye E being examined, there is provided a detector 80 comprising, for example, linear solid state image pickup elements. The image of the external-eye-part reflected by an illuminating light source 81 placed in front of the eye E being examined may be directed to the detector 80.

In this eye-fundus camera, the illuminating light source 61 and the photographing light source 64 are substantially conjugate with respect to the condenser lens 63a and, during observation, the observation light source 61 is turned on and during photography, the photographing light source 64 is momentarily turned on. The light source image is once formed near the ring slit plate 66 by the condenser lens 63b, and then the image of the annular opening of the ring slit plate 66 is formed near the apertured mirror 68 by the relay lenses 67a and 67b and there, the illuminating light is reflected and travels to the left. The eye fundus Ef is illuminated after the image of the annular opening has been formed near the cornea of the eye E being examined by the objective lens 70.

The reflected light from the eye fundus Ef travels to the right and is once imaged by the cornea and the objective lens 70, whereafter it passes through the apertured mirror 68 and is imaged by the focusing lens 71 and the photographing lens 72. During observation, the eye fundus image is directed upwardly by the jump-up mirror 73 which is in its solid-line position, and is observed by a TV monitor, not shown, through the image pickup tube 79, and during photography, the jump-up mirror 73 is rotated to its dotted-line position and the eye fundus image is formed on the photographing film 75 via the opened shutter 74. On the other hand, the reflected image of the external-eye-part formed by the light flux of the illuminating light source 81 is reflected by the beam splitter 69 and is imaged on the detector 80, and by the detector 80 having a linear detection range, the image of the external-eye-part is detected as a shape A which vertically crosses the eye E being examined as shown in FIG. 9.

Figure 9:
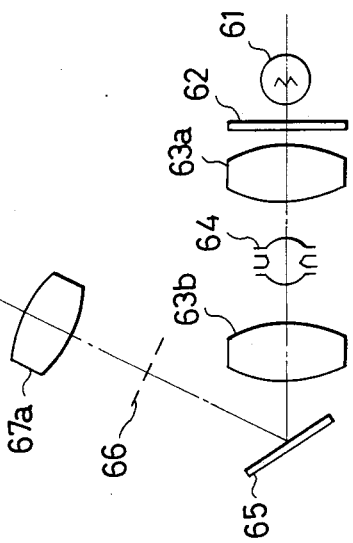
FIG. 9 illustrates the pupil in a state in which the eyelid has been fully raised and the detection range thereof.
Figure 10:
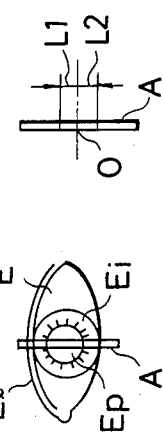
FIG. 10 illustrates the size of the pupillary zone in FIG. 9.

FIG. 9 shows a state in which the eyelid El is sufficiently raised, and the size of the pupil Ep encircled by iris Ei is measured by the detector 80. At this time, the size of the pupillary zone is judged as a length as shown in FIG. 10, and becomes L1 and L2 above and below the center O thereof, respectively, L1 and L2 being substantially equal to each other.

Figure 11:
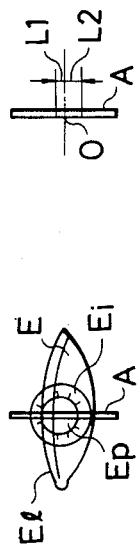
FIG. 11 illustrates the pupil in a state in which the eyelid has lowered and the detection range thereof.
Figure 12:
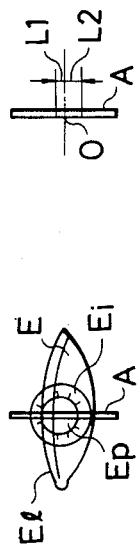
FIG. 12 illustrates the size of the pupillary zone in FIG. 11.

FIG. 11 shows a state in which the eyelid El has lowered and in this state, the pupillary zone is such that as shown in FIG. 12, the upper length L1 with respect to the center O is small as compared with the lower length L2. This means that the manner in which the eyelid El of the eye E being examined hangs may be determined by arbitrarily setting $L1/L2 = k(\leq 1)$. This closed state of the eyelid is detected, for example, immediately before the light emission of the photographing light source 64 to stop the light emission or may be displayed in the form of the reliability coefficient of the image obtained on the photographing film 75. Also, this reliability coefficient may be measured at the moment of light emission. As regards the beam splitter 69, it may be made movable as an ordinary mirror or may be made separate from the wavelength range of the body as a dichroic mirror capable of effecting wavelength division.

In this embodiment, the detector as means for measuring the size of the pupil Ei may be a length measuring system or an area measuring system using an area-type image pickup element or image pickup tube, and the display means thereof may be TV observation by the projection onto the finder or the image pickup tube.

Figure 13:
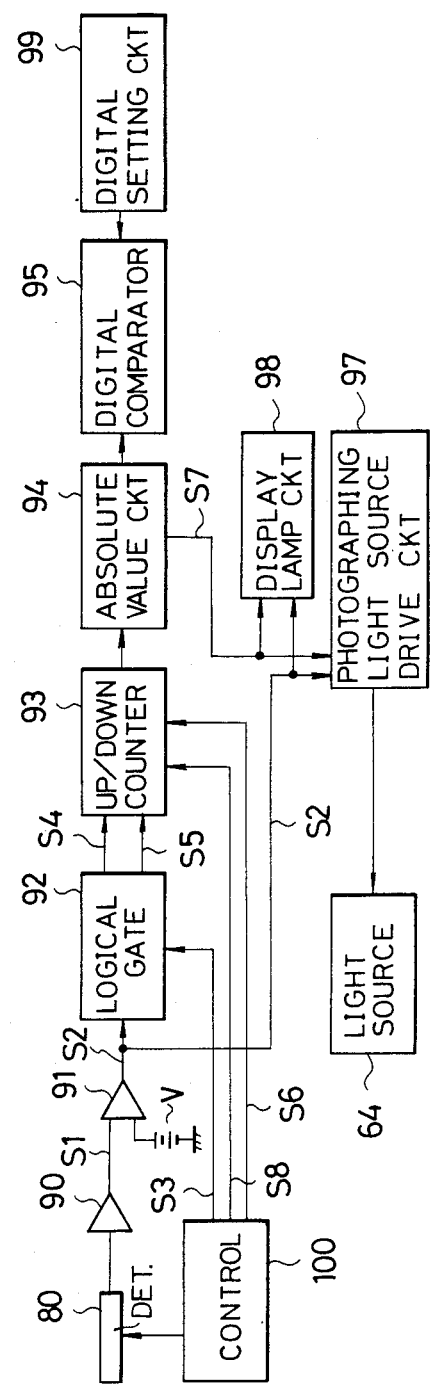
FIG. 13 is a block diagram of an electrical control circuit.

FIG. 13 shows an embodiment of an electrical control circuit of the present instrument. The output of the detector 80 is series-connected to an amplifier 90, an analog comparator 91, a logical gate 92, an up/down counter 93, an absolute value circuit 94 and a digital comparator 95. A threshold voltage V is also input to the analog comparator 91, the output of the digital comparator 95 is delivered to a photographing light source drive circuit 97 and a display lamp circuit 98, and the output of the photographing light source drive circuit 97 is connected to the photographing light source 64. The set output from a digital setting circuit 99 is connected to the digital comparator 95, the control output from a control circuit 100 is delivered to the detector 80, the logical gate 92 and the up/down counter 93, and part of the output of the analog comparator 91 is delivered to the photographing light source drive circuit 97 and the display lamp circuit 98.

Figure 14:
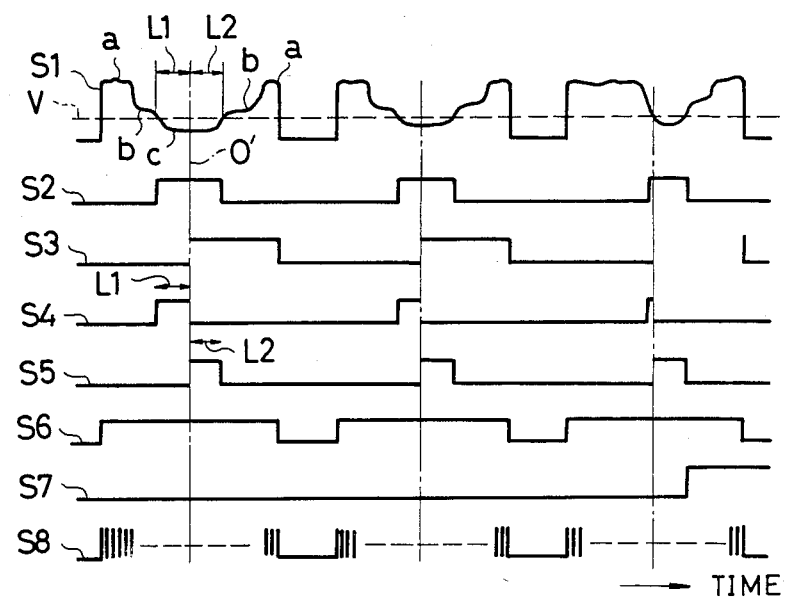
FIG. 14 is a timing chart thereof.

FIG. 14 is a timing chart of the electrical control circuit shown in FIG. 13. Signal S1 is the output waveform of the external-eye-part imaged on the detector 80. The eyelid El is good in reflection factor and bright and therefore assumes a high level as indicated at a, the intermediate b is the level of the iris Ei, and c is the level of the darkest pupil Ep. O' is the position on the detector 80 which corresponds to the center O of the optic axis, and L1 and L2 are the upper and lower lengths, respectively, of the pupillary zone shown in FIGS. 10 and 12. The threshold voltage V is set to a value somewhat higher than the level c of the pupil Ep, and signal S2 is one obtained by inputting the signal S1 of the external-eye-part to derive only the level c. Signal S3 is a signal which is obtained from the control circuit 100 and which assumes a Hi level of the timing corresponding to the center O of the optic axis, and S4 and S5 are signals obtained by changing over the signal S2 by the signal S3. Signal S4 is a signal for setting the up/down counter 93 to the up count mode and signal S5 is a signal for setting the up/down counter 93 to the down count mode. Only when signals S4 and S5 are at a Hi level, the counter 93 effects up count or down count. Signal S6 is a signal for resetting the counter 93, and resets the counter 93 when there is no output of the detector 80. Signal S7 is a signal which compares the value of the absolute value circuit 94 with the value of the digital setting circuit 99 by the digital comparator 95 and assumes a Hi level when the value from the absolute value circuit 94 is greater, and signal S8 is a clock pulse train put out for each element of the detector 80.

Operation of this circuit will now be described. The detector 80 continuously puts out the signal S1 of the external-eye-part. The signal S2 of only the pupil Ep is extracted from the signal S1 by the comparator 91 and is divided into two signals S4 and S5 by the logical gate 92. By these two signals S4 and S5, the counter 93 is caused to operate in the following manner. When the eyelid El is at a normal position, that is, when the eyelid is open, L1 and L2 are substantially equal to each other and therefore, during the time that signal S4 is at a Hi level, the counter 93 counts up and, when signal S5 assumes a Hi level, the counter 93 counts down, and if L1=L2, the value of the counter 93 becomes O. Actually, however, the output of the counter 93 rarely becomes O, and it would be suitable to set the value of $\Delta$, i.e., $|L1-L2| \leq \Delta$ which is in an allowable range, in the digital setting circuit 99 and judge the open state of the eyelid within the allowable range. When $|L1-L2| > \Delta$, a Hi level such as signal S7 is put out from the digital comparator 95 and at this time, the eyelid El is being closed or the center O of the optic axis and the position of the pupil Ep deviate from each other and therefore, an inhibiting operation can be exerted on the photographing light source drive circuit 97 to thereby stop the light emission of the photographing light source 64.

When the eyelid is in its fully closed state, position signal S2 of the pupil Ep continues to assume a Lo level and the operation of the photographing light source drive circuit 97 is stopped. At this time, the display lamp 98 is turned on by signals S7 and S2 to inform the photographer of the deviation of the eyelid El or the pupil Ep.

Figure 15:
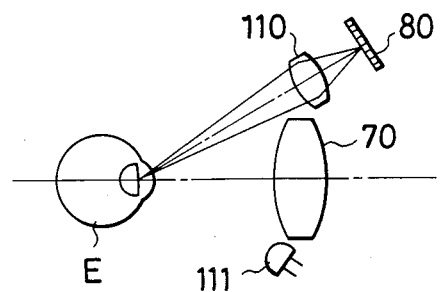
FIG. 15 shows another optical arrangement for detecting the pupillary zone.
Figure 16:
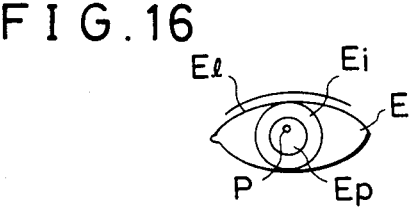
FIG. 16 illustrates a state in which the eyelid has been fully raised.
Figure 17:
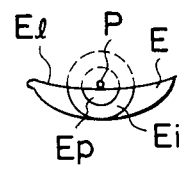
FIG. 17 illustrates a state in which the eyelid has lowered.

FIG. 15 shows another embodiment of the external-eye-part detecting optical system. The corneal reflection image P of an illuminating light source 111 in the eye E being examined which is illuminated by the light source 111 may be projected onto the detector 80 by a projection lens 110 disposed outside the optic axis of the objective lens 70. In this case. if the positional relation between the eye E being examined and the objective lens 70 is proper, by the detector 80 being disposed so as to monitor a certain predetermined position of the pupillary zone, i.e., the portion of the pupil on which the corneal reflection image P of the light source 111 is formed, the corneal reflection image P can be detected by the detector 80 as shown in FIG. 16 in the fully raised state of the eyelid El. On the other hand, when the eyelid El has lowered, as shown in FIG. 17, the corneal reflection image P is hindered by the eyelid El and cannot be sufficiently inferred. Accordingly, by detecting this corneal reflection image P, it becomes possible to detect the state of the eyelid El, whereby it becomes possible to stop the photographing function in accordance with the original measurement or as required. Here, the means for measuring the length of the pupillary zone shown in FIG. 8 can also be used jointly.

FIG. 18 shows the construction of a third embodiment of the present invention. Reference numeral 91 designates an observation light source comprising a tungsten lamp or the like. The light emitted from this observation light source 91 enters a mirror 95 through a condenser lens 92a, an infrared filter 93, a photographing light source 94 comprising a xenon discharge tube or the like, and a condenser lens 92b, is deflected by the mirror 95 and arrives at an apertured mirror 98 via a ring slit plate 96 and relay lenses 97a and 97b. The light having entered the apertured mirror 98 from the above-described illuminating optical system is reflected toward the eye E being examined by the apertured mirror 98, illuminates the fundus Ef of the eye E being examined, travels back along the original optical path and further passes through the apertured mirror 98 to the observation optical system. An objective lens 99 is disposed between the apertured mirror 98 and the eye E being examined, and a focusing lens 100, a photographing lens 101, a jump-up mirror 102, a shutter 103 and a photographing film 104 are successively arranged behind the apertured mirror 98 along the optic axis. On the opposite side of the jump-up mirror 102, a field lens 105 placed at a position conjugate with the photographing film 104, a mirror 106 for changing the optical path, a TV lens 107 and an image pickup tube 108 are successively disposed along the optic axis.

Also, an illuminating light source 109 for detecting the eyelid is disposed at one side of the objective lens 99, and along the emergent optical path thereof toward the eye E being examined, a mask plate 110 having a slit-like opening 110a as shown in FIG. 19 and a photographing lens 111 are disposed in succession, and the reflected light from the front-eye-part of the eye being examined enters an image receiving lens 112 disposed symmetrically with respect to the illuminating light source 109 with the objective lens 99 interposed therebetween and also enters a line sensor 113.

In this eye-fundus camera, the illuminating light source 91 and the photographing light source 94 are substantially conjugate with respect to the condenser lens 92a and, during observation, the observation light source 91 is turned on and during photography, the photographing light source 94 is momentarily turned on. The light source image is once formed near the ring slit plate 96 by the condenser lens 92b, and then the image of the annular opening of the ring slit plate 96 is formed near the apertured mirror 98 by the relay lenses 97a and 97b and there, the illuminating light is reflected and travels to the left. The eye fundus Ef is illuminated after the image of the annular opening has been formed near the cornea of the eye E being examined by the objective lens 99.

The reflected light from the eye fundus Ef travels to the right and is once imaged by the cornea and the objective lens 99, whereafter it passes through the apertured mirror 98 and is imaged by the focusing lens 100 and the photographing lens 101. During observation, the eye fundus image is directed upwardly by the jump-up mirror 102 which is in its solid-line position and is made into an image by the image pickup tube 108 through the TV lens 107 and, during photography, the jump-up mirror 102 is rotated to its dotted-line position and the eye fundus image is formed on the photographing film 104 via the opened shutter 103.

The optical system from the illuminating light source 109 to the line sensor 113 is for detecting a nictitation, and the eyelid detecting light flux emitted from the illuminating light source 109 is made into a slit-like light flux by the photographing lens 111 via the slit 110a of the mask plate 110 and illuminates the iris of the eye E being examined, as shown in FIG. 20. The reflected light of the slit illuminating light on the iris Ei is projected onto the line sensor 113 through the image receiving lens 112. The slit illuminating portion P1 on the iris Ei is imaged at a position Q1 on the line sensor 113. Assuming that the eye E being examined has nictitated, the slit illuminating portion moves to the eyelid El and the position at which the slit illuminating portion P2 on the eyelid El is imaged on the line sensor 113 shifts to Q2 as shown in FIG. 21. Accordingly, due to the nictitation, the illuminating portion on the line sensor 113 shifts from Q1 to Q2 and is detected as a movement on the coordinates on the line sensor 113. This signal may be displayed as an alarm such as emitted light or generated sound by display means, not shown, or can be connected to means for stopping the light emission of the photographing light source 94.

The above-described system is a nictitation detecting mechanism and can be used also as the alignment mechanism of an eye-fundus camera. That is, the distance between the eye E being examined and the objective lens 99 directly corresponds to the image position on the line sensor 113 and, by presetting the position, it is possible to judge the propriety of that distance. This distance can also be displayed on separate display means, for example, the display means on a TV monitor.

Also, in the above-described embodiment, the projection of the eyelid detecting illuminating light from the illuminating light source 109 is effected without using the objective lens 99, but such illuminating light may also be projected and received through the objective lens 99. FIG. 22 shows an embodiment in the latter case. The light flux emitted from an illuminating light source 109 may become a slit light via a mask 110 and a photographing lens 111 and may form a slit illuminating portion on the eye E being examined via an objective lens 99. The reflected image of this illuminating portion passes to a line sensor 113 via a deflecting mirror 114 and a slit opening 115 which are disposed immediately behind the objective lens 99 and thus, the light flux is projected onto an image receiving position Q1 or Q2. Also, in this embodiment, the iris Ei is used as the projected position of the light flux, but the cornea can also be used as such position. Further, to distinguish the function of the present embodiment from that of an original eyefundus camera, it is of course possible that a light of a wavelength range different from that of the observation light source 91 or the photographing light source 94 used during observation or photography is used as the wavelength of the eyelid detecting light flux. Furthermore, the present invention is applicable not only to eye-fundus cameras but also to apparatuses for measuring the eye refractive power or apparatuses for measuring the shape of the cornea, and the utilization thereof for the selection or deletion of measured data is also conceivable.

According to the present invention, as described above, the nictitation detection level is not affected by the quantity of illuminating light to the eye fundus or the like and therefore accurate detection of nictitation can be accomplished and further, even if there occurs a nictitation after the photographing switch has been depressed, the photographing light source does not emit light and can inform the photographer that there has occurred a nictitation.

What is claimed is:

1. An opthalmic instrument having:
    illuminating means for illuminating an eye being examined with a variable quantity of illumination light;
    imaging means for imaging a predetermined portion of the eye being examined at a predetermined image plane position along an optical axis;
    first light receiving means for detecting the quantity of illuminating light directed to the eye being examined, second light receiving means for detecting the quantity of light reflected from a portion of the eye being examined during blinking of the eye, and operation means for comparing said quantity of reflected light detected by said second light receiving means with said quantity of illuminating light detected by said first light receiving means; wherein
    the second light receiving means is disposed on a first side of the optical axis and an upper eyelid of the eye being examined is the light reflecting portion and is located on a second side of the optical axis, opposite to the first side.

2. An ophthalmic instrument according to claim 1, wherein said first light receiving means is provided outside a maximum photographing light flux and the light receiving surface thereof faces in the direction opposite to the eye being examined.

3. An ophthalmic instrument according to claim 2, wherein said second light receiving means is disposed outside of the maximum illuminating light flux region.

4. An ophthalmic instrument according to claim 1, wherein said second light receiving means is provided outside a maximum photographing light flux and the light receiving surface thereof faces in the direction of the eye being examined.

5. An ophthalmic instrument according to claim 1, wherein said operation means effects comparison by finding the ratio between the outputs of said first and second light receiving means.

6. An ophthalmic instrument according to claim 1, wherein said operation means effects comparison by finding the difference between the outputs of said first and second light receiving means.

7. An ophthalmic instrument according to claim 1, wherein an alarm is generated to the photographer in response to the detection of said nictitation.

8. An ophthalmic instrument according to claim 1, wherein the operation of said illuminating means for photographing is inhibited in response to the detection of said nictitation.

* * * * *

UNITED STATES PATENT AND TRADEMARK OFFICE
CERTIFICATE OF CORRECTION

PATENT NO. : 4,762,410
DATED : August 9, 1988
INVENTOR(S) : KYOJI SEKIGUCHI, ET AL.

It is certified that error appears in the above-identified patent and that said Letters Patent is hereby corrected as shown below:

COLUMN 1

Line 4, "this" should read --This--.
Line 11, "winking" should read --winking,--.

COLUMN 11

Line 61, "eyefundus" should read --eye-fundus--.

COLUMN 12

Line 16, "opthalmic" should read --ophthalmic--.

Signed and Sealed this

Twenty-fifth Day of April, 1989

Attest:

DONALD J. QUIGG

Attesting Officer

Commissioner of Patents and Trademarks